United States Patent
Braue, Jr. et al.

(10) Patent No.: US 6,472,438 B1
(45) Date of Patent: Oct. 29, 2002

(54) ACTIVE TOPICAL SKIN PROTECTANTS CONTAINING S-330

(75) Inventors: Ernest H. Braue, Jr., Whiteford, MD (US); Millard M. Mershon, Bel Air, MD (US); Catherine R. Braue, Whiteford, MD (US); Ruth A. Way, Colora, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/872,095

(22) Filed: Jun. 1, 2001

Related U.S. Application Data

(60) Provisional application No. 60/209,337, filed on Jun. 2, 2000.

(51) Int. Cl.[7] .......................... A61K 31/02; A61K 31/08; A61K 47/00; A61K 7/42
(52) U.S. Cl. .......................... 514/759; 424/59; 514/723; 514/772; 514/789; 514/844; 514/845; 514/937; 514/939; 514/944
(58) Field of Search ..................... 424/59; 514/723, 514/759, 772, 789, 844, 845, 937, 939, 944

(56) References Cited

U.S. PATENT DOCUMENTS

| | | | |
|---|---|---|---|
| 4,649,037 A | 3/1987 | Marsh et al. | 423/338 |
| 5,607,979 A | 3/1997 | McCreery | 514/759 |
| 5,914,436 A | 6/1999 | Klabunde et al. | 588/205 |
| 5,990,373 A | 11/1999 | Klabunde | 588/200 |
| 6,057,488 A | 5/2000 | Koper et al. | 588/200 |
| 6,224,885 B1 | 5/2001 | Jenner | 424/401 |

OTHER PUBLICATIONS

Smith, et al., Jrnl. of the American Acad. of Dermatology, Vo. 32, No. 5, part 1, May 1995, pp. 765–776 , Sulfur mustard: Its continuing threat as a chemical warfare agent, the cutaneous lesions induced, progress in understanding its mechanism of action, its long–term health effectgs, and new developments for protection and therapy.

Arroyo, et al., Jrnl. of Pharm. and Toxicol. Methods, vol. 33, No. 2, Apr. 1995, pp. 109–112, EPR/Spin–Label Technique as an Analytical Tool for Determining the Resistance of Reactive Topical Skin Protectants (rTSPs) to the Breakthrough of Vesicant Agents.

*Primary Examiner*—Shelley A. Dodson
(74) *Attorney, Agent, or Firm*—Elizabeth Arwine

(57) ABSTRACT

A topical skin protectant formulation containing a barrier cream and a reactive moiety for protecting warfighters and civilians against all types of harmful chemicals, specifically chemical warfare agents (CWA's). The topical skin protectant offers a barrier property and a reactive moiety that serves to neutralize chemical warfare agents into less toxic agents.

21 Claims, 3 Drawing Sheets

Figure 1. Active Topical Skin Protectant (aTSP) Decision Tree Network (DTN)

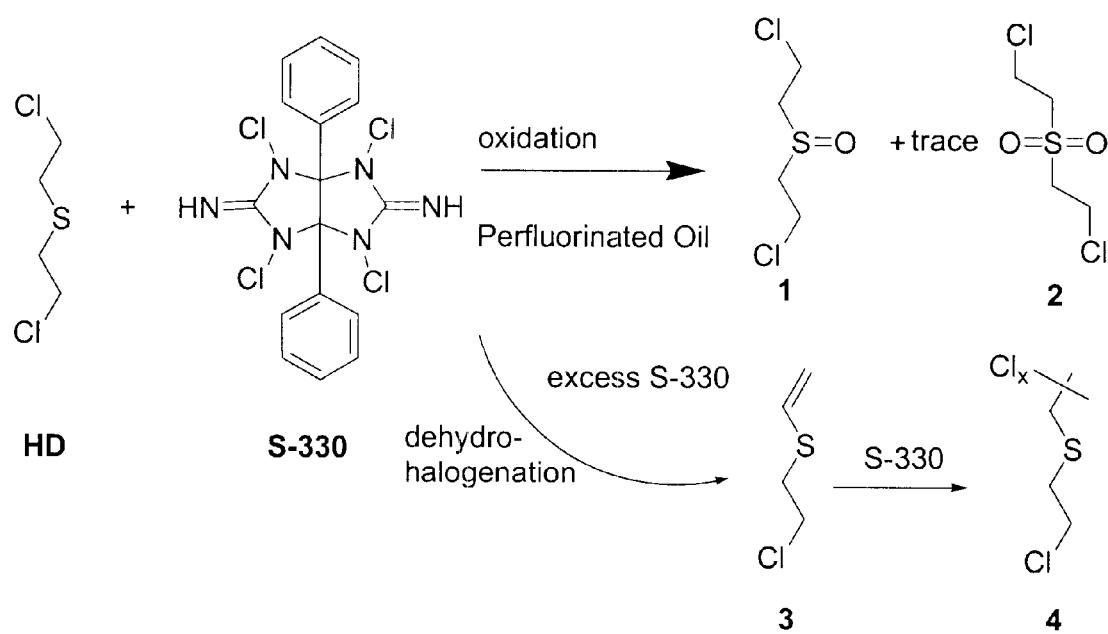
Figure 2. Reaction of HD with S-330 to produce the HD sulfoxide

Weanling Pig HD Vapor Test
ICD # 2701 (S-330) at 0.1 mm

No TSP
ICD2289
0.2 mm

| | Control | TSP | 15 min | 30 min | 45 min | 60 min |
|---|---|---|---|---|---|---|
| Series1 | 7.71 | 4.15 | 0.98 | 1.98 | 3.9 | 5.97 |

Erythema Index

Figure 3. Weanling pig test results for ICD2701 exposed to HD vapor for 15-60 minutes

ACTIVE TOPICAL SKIN PROTECTANTS CONTAINING S-330

PRIORITY INFORMATION

This application claims the benefit of priority of U.S. Provisional Application No. 60/209,337 filed Jun. 2, 2000.

BACKGROUND OF THE INVENTION

1. Field of the Invention

This invention relates to active topical skin protectants. More specifically, the invention relates to an active barrier cream for protection against all types of harmful chemicals, specifically chemical warfare agents (CWA's). The active barrier cream is applied prior to exposure on the skin of persons at risk of exposure to harmful chemicals to provide a protective barrier for the skin. The active barrier cream chemically or physically reacts with harmful chemicals such as CWA's (vesicants and nerve agents) to neutralize these harmful chemicals while the barrier properties of the cream prevent penetration of harmful chemicals through the cream to the skin.

2. Description of Related Art

The concept of applying a topical protectant to vulnerable skin surfaces before entry into a chemical combat arena has been proposed as a protective measure against percutaneous CWA toxicity since the first use of CWA's in World War I. The protectant would be applied to vulnerable skin surfaces prior to entry into a chemical combat area. Topical protectants should augment the protection afforded by the protective over garments and/or redefine the circumstances requiring mission oriented protective posture (MOPP) levels. The rapid action of vesicating agents, also known as blistering agents, such as sulfur mustard (HD) and lewisite (L), require a pre-exposure skin protection system or a contamination avoidance approach that may preclude the percutaneous toxicity of these agents. These approaches also reduce the risk of exposure to organophosphorus (OP) chemical agents (nerve agents) that unlike the vesicating agents, are lethal in droplet amounts.

An organic molecule, S-330, that reacts with CWA's was incorporated into a product and fielded as the M-5 ointment kit at the end of World War II (Formula 1).

Formula 1. S-330

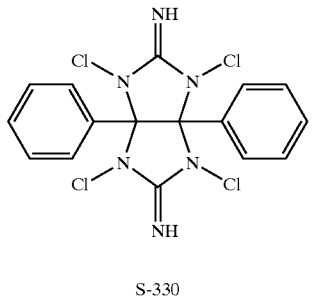

S-330

However, the unacceptable barrier properties and the undesirable cosmetic properties (that is foul odor and sticky texture) caused the cancellation of this product.

Two non-active topical skin protectant (TSP) formulations were developed at the United States Army Medical Research Institute of Chemical Defense (USAMRICD) and were transferred to advanced development following a Milestone Zero (MSO) Review in October 1990. The timeline of the approval of the TSP continued with MSI in 1993, a Investigational New Drug (IND) filed with the Food and Drug Administration (FDA) in 1994, MSII in 1995, and culminated with New Drug Application (NDA) approval in February 2000. The formulation described in McCreery U.S. Pat. No. 5,607,979 is directed to a topical skin protectant cream that acts as a barrier to CWA's.

Although the TSP in McCreery's formulation extends the protection afforded by MOPP and allows a longer window for decontamination, it does not completely remove the possibility for contamination because the CWA is not neutralized. To avoid contamination of other areas of the battlefield and to preclude the future percutaneous absorption of the CWA, decontamination is still required. Furthermore, although the McCreery formulation provides excellent protection against GD and HD liquid, its protection against HD vapor is minimal.

To overcome these deficiencies, there is a need for a new TSP that contains an active component. This active Topical Skin Protectant (active TSP) was developed within the following criteria. First, the active TSP should neutralize CWA's including but not limited to sulfur mustard (HD), soman (GD), and VX. Second, the barrier properties of the TSP should be maintained or increased. Third, the protection against HD vapor should increase. And fourth, the cosmetic characteristics (i.e., odor, texture) of the TSP should be maintained.

This invention meets the above criteria and solves the problems associated with the past TSP's by providing an active topical skin protectant that increases effectiveness of the TSP barrier quality and neutralizes CWA's into less harmful products.

It is therefore, an objective of the present invention to provide an active topical skin protectant that prevents the percutaneous absorption of CWA's and converts these toxic materials into less harmful products.

It is a further objective of the present invention to provide an active topical skin protectant that maintains desirable cosmetic properties making it acceptable to the user. Specifically, the active TSP should not be sticky, have no offensive odor, and should be non-irritating to the skin.

It is still a further objective of the invention to provide an active topical skin protectant that is practical for field operations. Specifically, the active TSP should have a stable shelf life, not be easily washed off with water, and should not react with insecticides or camouflage paint.

SUMMARY OF THE INVENTION

A topical skin protectant formulation for neutralizing chemical warfare agents into less toxic products comprising: a barrier base cream, and one or more active moieties. The base cream comprises poly(tetrafluoroethylene) (PTFE) resins dispersed in perfluorinated polyether oils (PFPE). An active moiety that has been found to be very effective with the base cream is S-330. Effective formulations containing S-330 and other active materials in the base cream are listed in Table 1. The active barrier cream is applied to the skin prior to exposure of persons at risk of exposure to harmful chemicals to provide an active barrier to protect the skin. The active barrier cream chemically or physically reacts with harmful chemicals such as CWA's to neutralize these harmful chemicals while the barrier properties of the cream prevent penetration of harmful chemicals through the cream to the skin.

BRIEF DESCRIPTION OF THE DRAWINGS

FIG. 1. Flow diagram of the active TSP Decision Tree Network for efficacy evaluation.

FIG. 2. Reaction of HD with S-330 to produce the HD sulfoxide.

FIG. 3. Weanling pig test results for ICD2701 exposed to HD vapor for 15–60 minutes.

DETAILED DESCRIPTION

Candidate Active Moieties

The types of materials that neutralize harmful agents use three main modes of action: oxidation, reduction or hydrolysis.

The selection of the active materials, however, is restricted by operating criteria. Thus, the active moiety must not irritate the skin, react with insecticides or camouflage paints or be unstable. This restriction eliminates many of the most active species. Furthermore, the active moiety must be incorporated into a highly fluorinated environment that is not amenable to many reaction pathways.

Table 1 is a list of formulations containing S-330 and other active materials that are acceptable for use in the present invention:

TABLE 1

LIST OF FORMULATIONS CONTAINING S-330 AND OTHER ACTIVE MATERIALS FOR ACTIVE TOPICAL SKIN PROTECTANTS

| ICD # | Active Moiety | % Active | % other | % PFPE | % PTFE |
|---|---|---|---|---|---|
| 2650 | S-330 | 10 | | 15 11 90 | |
| 2701 | S-330 | 10 | | 54 | 36 |
| 2702 | S-330 | 10 | light surfactant (2853) 50 | | 40 |
| 2972 | S-330 | 10 | | 90 | |
| 3310 | S-330 | 5 | | 94.4 | 0.0 |
| 3354 | S-330 | 10 | | 54 | 36 |

Abbreviations:
S-330: 1,3,4,6-tetrachloro-7,8-diphenyl-2,5-diimino glycoluril (ICD2703) available from Sigma-Aldrich, Milwaukee, WI
PTFE: polytetrafluoroethylene available as FSA powder from Ausimont, Morristown, NJ
PFPE: perfluoropolyether available as FOMBLIMTM Y25 oil from Ausimont, Morristown, NJ
ICD2853 light PFPE Surfactant, Krytox ®, CAS #60164-51-4 Dupont, Wilmington, DE
ICD2289 50% PTFE, 50% PFPE, same formulation composition as ICD3004 and SERPACWA (Skin Exposure Reduction Past Against Chemical Warfare Agents)
ICD1511 30% PTFE (L-206 powder from Ausimont) and 70% YR PFPE (as FOMBLIMTM ™ YR oil from Ausimont)
Percentages are in weight percentages Formulations 2650, 2701, 2702, and 2972 in Table I were mixed with high sheer. Formulations 3310 and 3354 were mixed by simple mechanical mixing.

All formulations listed above are useful for both liquid and vapor challenges. The amount of S-330 varies with formulations. S-330 is dispersed as a mixture of fine powder in the base cream. The object is to optimize the quantity of S-330 in the base cream without losing the barrier properties of the base cream. The amount of S-330 can vary from about 1–30%. The amount of perfluorinated polyether oil can vary from about 40 to 60%. The amount of polytetrafluoroethylene can vary from about 30 to 50%.

One criterion for the selection of the active materials is increased efficacy against HD vapor. The best candidate compound is S-330. It is a Chloramide with the chemical name 1,3,4,6-tetrachloro-7,8-diphenyl-2,5-diimino glycoluril. Compound S-330 is very effective against HD and is relatively non-irritating to the skin. It reacts with HD by different mechanisms, depending on the formulation. This compound has been formulated into many candidate active TSPs (Table 1).

Identification of a neutralization system is not sufficient. The active moiety must also be incorporated into the TSP matrix without degradation of the barrier properties.

The basic base cream in the TSP material is ICD2289 consisting of fine particulates of polytetrafluoroethylene resins dispersed in perfluorinated polyether oils. The excellent barrier properties of this high molecular weight polymer formulation are related to the low solubility of most materials in it. Only highly fluorinated solvents like Freon® have been observed to show appreciable solubility. This aprotic non-polar polymer mixture provides a unique medium for the active moieties of the invention. Reaction mechanisms that do not involve charged transition states should be favored in this chemical environment.

Base creams formed from about 35–50% fine particulates of certain poly(tetrafluoroethylene) PTFE resins dispersed in perfluorinated polyether oils (PFPE) having viscosities from about 20 cSt to about 500 cSt afford good protection against chemical warfare agents such as HD, L, sulfur mustard/Lewisite mixtures (HL), pinacolyl methylphosphonofluoridate (soman or GD), thickened soman (TGD) and O-ethyl S-(2-diisopropylaminoethyl)methylphosphonothiolate (VX). PTFE and PFPE are available commercially from Ausimont (Morristown, N.J.) and Dupont (Wilmington, Del.).

The base creams used in the invention are suspensions of 35–50% finely divided PTFE having a surface area below about 6 $m^2/g$ in a perfluorinated polyether base oil prepared from perfluoropropylene oxide, which has a viscosity between about 20 and about 500cSt. More preferred compositions comprise from about 35% to about 50% of finely divided PTFE having an average particle size from about 0.1 $\mu$m to about 10 $\mu$m and a surface area below about 4 $m^2/g$ in a perfluorinated polyether base oil from 40% to 60% having a viscosity between about 20 and about 500 cSt.

Suitable perfluorinated polyether oils are Fomblin® HC- and Y-oils (Ausmont) and Krytox.® oils (Dupont). The Fomblin® oils are mixtures of linear polymers based on perfluoropropylene oxide having the following chain structure: $CF_3$—$[(OCF(CF_3)CF_2)_n$—$(OCF_2)_m]OCF_3$. The Krytox® oils are mixtures of linear polymers also based on perfluoropropylene oxide and have the chemical structure F—$[(CF(CF_3)CF_2O]_mCF_2CF_3$. Fomblin® Z oils having the formula: $CF_3$—$[(OCF_2CF_2)_n$—$(OCF_2)_m]$—$OCF_3$ may also be useful in the practice of the invention. The indices n and m indicate the average number of repeating polymeric subunits in the oil molecules. The oils may have a viscosity of about 20 cSt to about 500 cSt or more. The creams were generally prepared according to U.S. Pat. No. 5,607,979, incorporated herein in its entirety.

As mentioned earlier, a criterion for the active TSP is the maintenance of the barrier properties of the base cream. Solid particulates of active moiety must be small enough so that crystalloid structures do not provide small channels that allow liquid CWA's through the 0.1 to 0.2 mm thick barrier coating. Ball mill grinding and solvent dissolution techniques may be used to reduce the particle size in the inventive formulation. Further, the PTFE must not have large crystals for the same reason. Other additives to the base cream may be water and surfactant. The surfactant facilitates the mixing of the water with the base cream. An example of a typical surfactant is perfluoropolyalkylether (Krytox® CAS # 60164-51-4 from Dupont). Additional materials may also be incorporated as long as they do not reduce effectiveness of the topical protectant, such as stabilizers, camouflage paints, and sunscreens.

A further understanding of the composition of the topical protectant of the invention can be obtained by reference to certain specific example formulations set forth in Table 1. These examples are provided herein for purposes of illustration only and are not intended to be limiting.

Temperature and mixing sheer should be monitored to maintain the base cream at the desired consistency and quality. To prepare mixtures, a quantity of base oil was carefully weighed in a small vial and the weight of PTFE and active moiety needed for preparation of the desired formulation was weighed out on glassine weighing paper. The solid powders were then slowly mixed into the oil in the vial using a small glass stirring rod. Mixing was slow and deliberate at first to reduce loss of fine particulates into the air. After this initial process, complete mixing of the components in the formulation was achieved by using a mechanical stirrer under low shear or by using a Polytron Mixer (Brinkmnann Instruments) under very high shear. Mixing with the Polytron used a medium head at the setting of 5 for not less than five minutes. During the Polytron mixing process the vial got warm. The vial temperature was not allowed to get above what could be comfortably held in the hand. This was achieved by stopping the mixing process until the vial cooled or else the vial was placed in a cool water bath. Which ever method was used, the total high shear mixing time was always at least five minutes.

Water Component

Many active moieties require the presence of water as a reagent for the hydrolysis of HD and GD. The reactive moieties that react by a hydrolysis mechanism require the presence of water. When the topical protectant is applied to the skin of a user, moisture in the form of perspiration may also aid in the hydrolysis of HD and GD. The addition of perfluorinated polyether surfactants to the base cream facilitates the addition of water. One of the example formulations listed in Table 1 contains a surfactant. Water and surfactant were often added when S-330 was used in combination with other candidate active moieties.

Multilayer Approach

Although an active TSP can be generally the application of a powder that is a POM/RNP sprinkled on the skin, or an active moiety in a base cream wherein the cream is spread on the skin, a multilayering approach can also be used. The multilayer approach would be to use the active TSP as the first layer and a solid active moiety powder as the second layer. The second layer would be a thin coating of the solid active moiety powder sprinkled over the active TSP cream. This approach would provide a concentrated decontamination material at the surface of the barrier cream, which would accelerate the neutralization process of CWA's coming in contact with the surface. In the alternative, the solid active moiety powder can be applied first followed by an application of the active TSP.

Testing

Evaluation of formulations was conducted with a decision tree network (DTN). FIG. 1 shows the active topical skin protectant (active TSP) decision tree network which is a flow chart describing the path that active TSPs follow during efficacy evaluation. The DTN is divided into two pathways: one for vesicants and the other for nerve agents. Within these pathways there are three blocks each with a decision point. The first block consists of a series of three in vitro modules, the second block consists of in vivo modules, and the third block consists of an advanced animal module to determine the influence of time, water and interactions with other products.

The first block of modules includes three tests: the M8 paper test, the penetration cell test, and the proof-of-decon test. These tests are used to determine the initial efficacy of candidate formulations and to eliminate non-effective candidates before animal testing. The M8 paper test is used to evaluate the barrier resistance of liquid CWA challenges, including HD, pinacolyl methylphosphonofluoridate (soman, GD), and O-ethyl S-(2-diisopropylaminoethyl) methylphosphonothioate (VX). In this test a 0.15 mm layer of active TSP is placed over a well-defined area of M8 chemical detection paper and challenged with an 8$\mu$l droplet of CWA. When agent penetrates the active TSP barrier and reaches the M8 paper, a colored spot develops on the paper. The test assemblies are observed for 6 hours and the breakthrough time is reported for each sample. A total of nine replicates are run for each test, and a standard reference compound is included each day for quality control.

The penetration cell test is used to evaluate the barrier properties against both liquid and vapor CWA challenges. In this test the lower half of a Reifenrath diffusion cell (Reifenrath Consulting and Research, Richmond, Calif.) is used. A 0.15 mm thick layer of active TSP is supported by nitrocellulose paper on top of the cell. The active TSP layer is challenged with a 10-$\mu$l liquid droplet of HD or an 8 $\mu$l droplet of GD, or a saturated vapor cup of HD or GD. Breakthrough of CWA into the lower chamber of the diffusion cell is monitored using a miniature continuous air monitoring system (MINICAMS, CMS Research, Birmningham, Ala.). This system has been automated to allow continuous monitoring of five cells in a 40-min cycle. The test runs for 20 hours and the accumulated amounts of agent that break through the active TSP barrier are calculated. From these data, we obtained two values: the cumulative amount of CWA that penetrates through the active TSP, and the time at which a "breakthrough" occurs. We defined "breakthrough" values at the minimum amount of HD (1000 ng) and GD (1000 ng) that results in a physiological response. Minimal amount of HD for vesication equals 1000 ng. See F. R. Sidell, J. S. Urbanetti, W. J. Smith, and C. G. Hurst in *Textbook of Military Medicine, Medical Aspects of Chemical and Biological Warfare,* edited by F. R. Sidell, E. T. Takafuji, and D. R. Franz (Office of the Surgeon General at TMM Publications, Washington, D.C. 1997), p 201. $LD_{50}$ for soman (GD)=350 mg/70 kg man. See F. R. Sidell in *Textbook of Military Medicine, Medical Aspects of Chemical and Biological Warfare,* edited by F. R. Sidell, E. T. Takafuji, and D. R. Franz (Office of the Surgeon General at TMM Publications, Washington, D.C. 1997), p 141. These two values allow us to rank the active TSP formulations and to select the appropriate component for advanced development.

The proof-of-neutralization test is used to verify that active TSP formulations actually neutralize CWA's into less toxic materials. This test uses the head-space solid phase microextraction (HS-SPME) technique for the collection of CWA's. Samples collected on the extraction filament are analyzed by gas chromatography/mass spectroscopy. 100 mg of active TSP formulation are challenged with 0.1 ul of neat CWA (HD, GD, or VX) in a small vial. The head-space above the mixture is sampled periodically to determine the amount of CWA remaining in the flask. Efficacy is determined by the percent loss of CWA. Other analytical techniques such as Nuclear Magnetic Resonance (NMR) and Fourier-Transform Infrared Spectrometry (FTIR) have also been used in this module.

Formulations that pass this initial set of screens are moved into the second phase of testing using animal models. The weanling pig test for HD vapor evaluates a 0.10 mm thick layer of active TSP spread on the depilated dorsa. The standard saturated vapor cup is used for a 15–60 min challenge. The effectiveness of the active TSP is determined by measuring the degree of erythema that developed on the skin exposure site. Erythema is measured objectively using a reflectance calorimeter.

The rabbit lesion area ratio (LAR) test is used to evaluate a challenge by HD liquid. In this test, a 0.10 mm layer of active TSP spread on the clipped dorsa is challenged with 1.0 µl of liquid HD. The effectiveness of the active TSP is determined by measuring the lesion areas of protected and non-protected sites.

The rabbit acetycholinesterase (AchE) inhibition test is performed by applying a 0.10 mm thick layer of active TSP on the clipped dorsa of rabbit followed by a fixed dose of GD (1 $LD_{50}$), TGD (1 $LD_{50}$), or VX (20 $LD_{50}$). The effectiveness of the active TSP is determined by lethality and also by measuring the erythrocyte acetycholinesterase activity 0.5, 1, 2, and 24 hours following exposure.

Candidate formulations that pass the in vivo test modules move into advanced animal testing. These tests are similar to the initial animal tests with the addition of stresses for wear-time and washing with water. Interactions with other products that a soldier might use are also evaluated. These products include camouflage paints, sunscreens and insecticides.

Example Formulation ICD2701

A major shortcoming of the non-active TSP currently in advanced development is its lack of efficacy against a HD vapor challenge. A significant improvement in the efficacy has been achieved by adding the active moiety S-330, to this formulation mixture. S-330 is a glycoluril with four active chlorine atoms. It neutralizes HD by oxidation (M. Shih, et al, J Appl Toxicol, Vol 19, S83–S88, 1999). The oxidation in PTFE oil is very rapid and completed in less than 4 minutes. In a large excess of S-330 (FIG. 2), the major products result from dehydrohalogenation and chlorination of the side chains (3, 4). At a high HD/S-330 ratio, the major product was HD sulfoxide 1 (FIG. 2). Under both conditions, only a trace of the HD sulfone 2, also a blistering agent, was observed.

Although S-330 reacts rapidly with HD, it does not react with nerve agents. This is not a serious limitation because other reactive components that are efficacious against nerve agents may be incorporated into the final product.

Results

The best formulation containing S-330 is ICD2701 (See formulation in Table 1 for S-330). This candidate formulation has gone through most of the DTN screening modules. The results of these tests are summarized in Table 2 below.

TABLE 2

Summary of active TSP DTN evaluations of ICD2701 and ICD3004

| TEST | ICD2701 | ICD3004 |
|---|---|---|
| M8 Paper, HD | >6 hr protection | >6 hr protection |
| Penetration cell, HD vapor | 60 ng in 20 hr[a] | 4,037 ng in 20 hr |
| Penetration cell, HD liquid | 1,000 ng in 481 min[a] | 1,000 ng in 240 min |
| Proof of decon, HD | <1% of control[a] | 100% of control |
| Weanling pig HD vapor | 60 min protection[a] | <15 min protection |
| Guinea pig HD vapor | 45–60 min protection[a] | <5 min protection |
| Rabbit LAR | 92% protection[a] | 79% protection |
| Rabbit LAR, time stress | 89% protection | N/A |
| Rabbit LAR, water stress | 98% protection | N/A |

TABLE 2-continued

Summary of active TSP DTN evaluations of ICD2701 and ICD3004

| TEST | ICD2701 | ICD3004 |
|---|---|---|
| GD AChE inhibition (1 $LD_{50}$) | 55% activity | 67% activity |
| TGD AChE inhibition (1 $LD_{50}$) | 66% activity | N/A |
| VX AChE inhibition (20 $LD_{50}$) | 66% activity | 77% activity |

[a]Significant (P = 0.05) improvement over ICD3004
N/A = not available

This formulation has significantly (P=0.05) increased protection compared to the non-active TSP (ICD3004) in six test modules for HD. In the weanling pig HD vapor test, ICD2701 dramatically improves efficacy. FIG. 3 illustrates these results. FIG. 3 illustrates the degree of erythema or redness as measured by the mean (±SEM) $\Delta a^*$reflectance values for positive control sites (no active TSP, 15-min challenge), quality control standard (0.2-mm thick ICD 2289 base cream, 15-min challenge). It should be noted that the thickness used for the standard is double that used by the active TSP. Experimentally this is done to achieve some protection with the standard. If the standard is spread at only a 0.10 mm thickness, no protection is observed for a 15 min challenge (see FIG. 3). The standard sites are included for quality control purposes. ICD2701 (0.1-mm thick) is challenged for 15, 30, 45 or 60 min. Thus, the active TSP is evaluated over a dosing time of 15–60 minutes. There were six animals per treatment group with four treatment sites per animal. All treatment groups were found to provide significantly (P=0.05, n=6) better protection than the positive control sites, which had no active TSP. The increased erythema following a saturated HD challenge of 1.4 $mg l^{-1}$ is denoted by the mean $\Delta a^*$reflectance values.

The results in FIG. 3 illustrate that ICD2701 provides excellent protection against 15 and 30 minute challenges, good protection against a 45 minute challenge, and some protection against a 60 minute challenge. Similar results are observed in the haired and hairless guinea pig models. The guinea pig models are useful in evaluating active TSPs but are not part of the DTN. These results represent a dramatic improvement over the non-active TSP. There is even a modest but statistically significant (P=0.05) improvement observed for ICD2701 in the liquid HD model (rabbit LAR test). The dramatic improvement is confirmed in both the penetration cell test and the HS-SPME proof-of-decon test (see Table 2).

Formulation ICD2701 is not expected to react with nerve agents; however, it is still important that the candidate formulation not lose efficacy against liquid nerve agent challenges. The data in Table 2 show that ICD2701 retains the good protection illustrated by ICD3004 against all the nerve agent tests. Remarkably, both formulations ICD2701 and ICD3004 protect against 20 $LD_{50}$ challenges of VX.

Having now fully described the invention, it will be apparent to one of ordinary skill in the art that many changes and modifications can be made thereto without departing from the spirit or scope of the invention as set forth herein.

What is claimed is:

1. A topical skin protectant formulation for neutralizing chemical warfare agents into less toxic products comprising: a barrier base cream; and 1,3,4,6-tetrachloro-7,8-diphenyl-2,5-diimino glycoluril as an active moiety.

2. A topical skin protectant formulation for neutralizing chemical warfare agents into less toxic products comprising a base cream, wherein the base cream comes poly (tetrafluoroethylene) resins dispersed in perfluorinated polyether oils; and 1,3,4,-tetrachloro-7,8-diphenyl-2,5-diimino glycoluril as an active moiety.

3. A topical skin protectant formulation comprising: about 10% 1,3,4,6-tetrachloro-7,8-diphenyl-2,5-diimino glycoluril and about 30% polytetrafluoroethylene and 60% perfluoropolyether.

4. The topical skin protectant formulation of claim 2, wherein the active moiety is present in an amount of 1–30%, the perfluoropolyether is present in an amount of 40–60%, and the polytetrafluoroethylene is present in an amount of 30–50%.

5. A topical skin protectant formulation comprising: about 10% 1,3,4,6-tetrachloro-7,8-diphenyl-2,5-diimino glycoluril about 54% perfluoropolyether and about 36% polytetrafluoroethylene.

6. A topical skin protectant formulation comprising: about 10% 1,3,4,6-tetrachloro-7,8-diphenyl-2,5-diimino glycoluril, about 50% light surfactant perfluoropolyether oil, and about 40% polytetrafluoroethylene.

7. A topical skin protectant formulation comprising: about 10% 1,3,4,6-tetrachloro-7,8-diphenyl-2,5-diimino glycoluril, and about 90% perfluoropolyether.

8. A topical skin protectant formulation comprising: about 5% 1,3,4,6-tetrachloro-7,8-diphenyl-2,5-diimino glycoluril, and about 95% perfluoropolyether.

9. A topical skin protectant formulation comprising: about 1–30% 1,3,4,6-tetrachloro-7,8-diphenyl-2,5-diimino glycoluril, about 40–70% perfluoropolyether and about 20–50% polytetrafluoroethylene.

10. A topical skin protectant formulation for neutralizing chemical warfare agents into less toxic products comprising: a barrier base cream, said barrier base cream comprising poly(tetrafluoroethylene) resins dispersed in perfluorinated polyether oils; and 1,3,4,6-tetrachloro-7,8-diphenyl-2,5-diimino glycoluril.

11. The topical skin protectant formulation of claim 10, further comprising one or more additives.

12. The topical skin protectant formulation of claim 11, wherein said additives comprise one or more of water, stabilizers, camouflage paints, and sunscreens.

13. A topical skin protectant system comprising:
  a) a topical skin protectant formulation for neutralizing chemical warfare agents into less toxic products comprising a barrier cream and 1,3,4,6-tetrachloro-7,8-diphenyl-2,5-diimino glycoluril as an active moiety for applying to skin, and
  b) a powder comprising 1,3,4,6-tetrachloro7,8-diphenyl-2,5-diimino glycoluril as a solid active moiety for applying on top or below of the skin protectant formulation.

14. A method of protecting a user against chemical warfare agents comprising:
  a) applying a thin layer of 1,3,4,6-tetrachloro-7,8-diphenyl-2,5-diimino glycoluril, and
  b) applying a layer of a topical skin protectant formulation for neutralizing chemical warfare agents into less toxic products comprising a barrier cream and 1,3,4,6-tetrachloro-7,8-diphenyl-2,5-diimino glycoluril.

15. A method of protecting a user against chemical warfare agents comprising:
  a) applying a layer of a topical skin protectant formulation for neutralizing chemical warfare agents into less toxic products comprising a barrier cream and 1,3,4,6-tetrachloro-7,8-diphenyl-2,5-diimino glycoluril; and
  b) applying a thin layer of 1,3,4,6-tetrachloro-7,8-diphenyl-2,5-diimino glycoluril on top of said layer of topical skin protectant formulation.

16. A method of protecting a user against chemical warfare agents comprising: applying a topical skin protectant formulation for neutralizing chemical warfare agents into less toxic products comprising: (a) a barrier cream and (b) 1,3,4,6-tetrachloro-7,8-diphenyl-2,5-diimino glycoluril as an active moiety.

17. A method of making a topical skin protectant formulation comprising: mixing 1,3,4,6-tetrachloro-7,8-diphenyl-2,5-diimino glycoluril as an active moiety with a barrier cream comprising poly(tetrafluoroethylene) resins dispersed in perfluorinated polyether oils.

18. A topical skin protectant formulation for neutralizing chemical warfare agents into less toxic products comprising: an active moiety, wherein said active moiety is 1,3,4,6-tetrachloro-7,8-diphenyl-2,5-diimino glycoluril.

19. The topical skin protectant formulation of claim 1, wherein said chemical warfare agents are one or more of the group consisting of blistering agents, G class nerve agents, and VX.

20. The topical skin protectant formulation of claim 19, wherein said blistering agent is sulfur mustard.

21. The topical skin protectant formulation of claim 19, wherein said G class nerve agent is soman.

* * * * *